United States Patent

Kleemann, Axel et al.

[11] 4,399,302
[45] Aug. 16, 1983

[54] 4-METHYLMERCAPTO-2-ACETOXY-BUTYRALDEHYDE

[75] Inventors: Kleemann, Axel, Hanau, Fed. Rep. of Germany; Rudolf Fahnenstich, Wykoff, N.J.; Marc Samson, Hanau, Fed. Rep. of Germany

[73] Assignee: Degussa Aktiengesellschaft, Frankfurt, Fed. Rep. of Germany

[21] Appl. No.: 352,451

[22] Filed: Feb. 25, 1982

[30] Foreign Application Priority Data

Feb. 25, 1981 [DE] Fed. Rep. of Germany ....... 3107007

[51] Int. Cl.³ ............................................ C07C 149/14
[52] U.S. Cl. .................... 560/266; 424/317; 560/238; 560/262; 562/581
[58] Field of Search ................... 560/266; 568/454, 41

[56] References Cited

U.S. PATENT DOCUMENTS 3,527,809  9/1970  Pruett et al. ........................ 560/266
3,773,927  11/1973  Cummins ............................ 424/166
4,052,461  10/1977  Tinker et al. ........................ 560/266

Primary Examiner—Vivian Garner
Attorney, Agent, or Firm—Cushman, Darby & Cushman

[57] ABSTRACT

The invention is directed to 4-methylmercapto-2-cacetoxy-butyraldehyde of the formula

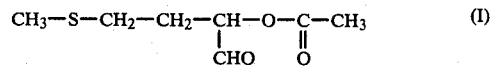

and a process for its production by hydroformylating 3-methylmercapto-1-acetoxy-propene-1 of the formula

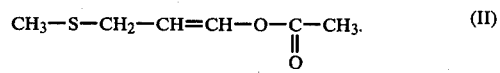

4-methylmercapto-2-acetoxy-butyraldehyde can be used as an intermediate product for the production of 4-methylmercapto-2-hydroxy-butyric acid, the hydroxy analogue of methionine.

1 Claim, No Drawings

4-METHYLMERCAPTO-2-ACETOXY-BUTYRALDEHYDE

SUMMARY OF THE INVENTION

The invention is directed to 4-methylmercapto-2-acetoxy-butyraldehyde of the formula

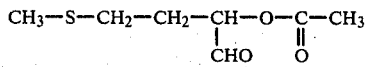
(I)

and a process for its production which is characterized by hydroformylating 3-methylmercapto-1-acetoxy-propene-1 of the formula

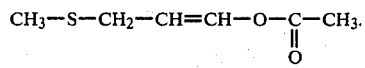
(II)

in a known manner in the presence of a rhodium complex which contains an organic compound of trivalent phosphorus as a ligand and in which the ligand is used in excess.

4-methylmercapto-2-acetoxy-butyraldehyde is a valuable intermediate product for a new "cyanide free" synthesis of 4-methylmercapto-2-hydroxy-butyric acid, the hydroxy analogue of the essential aminoacid methionine. The 4-methylmercapto-2-acetoxy-butyraldehyde can be readily converted into 4-methylmercapto-2-hydroxy-butyric acid by oxidation of the aldehyde group and hydrolytic splitting off of the acetoxy group. This substituted butyric acid in turn is a valuable, liquid material for supplementing mixed fodders with methionine (see e.g. Cummins U.S. Pat. No. 3,773,927).

The 4-methylmercapto-2-acetoxy-butyraldehyde of the invention is a colorless liquid which boils at 78° C. at a pressure of 0.13 mbar. It is produced according to the invention by reacting 3-methylmercapto-1-acetoxy-propene-1 with carbon monoxide and hydrogen in the presence of a rhodium complex which contains an organic compound of trivalent phosphorus as ligand. It is surprising in this case that a sulfur containing starting material is at all accessible to the known hydroformylation in the presence of a rhodium catalyst since sulfur compounds normally react very readily with rhodium catalysts and thereby reduce their activity.

The 3-methylmercapto-1-acetoxy-propene-1 employed for the hydroformylation reaction in turn can be produced by reacting 3-methylmercaptopropionaldehyde in the presence of a catalytic amount of an acid with isopropenyl acetate or else with acetic anhydride and sodium acetate and isolating the 3-methylmercapto-1-acetoxy-propene-1 formed by distillation.

Surprisingly there does not occur the formation of the likewise to be expected isomer 3-methylmercapto-2-acetoxy-methyl-propionaldehyde as a byproduct in the hydroformylation.

An especially high selectivity of the hydroformylation reaction in the direction of the desired 4-methylmercapto-2-acetoxy-butyraldehyde is produced by using a complex compound of rhodium as the catalyst. Such catalyst systems can be employed in a suitable solvent or rather, in using an insoluble polymeric ligand, as solid material.

In a preferred illustrative form of the process of the invention the 3-methylmercapto-1-acetoxy-propene-1 is reacted with carbon monoxide and hydrogen in a molar ratio of $CO:H_2$ between 10:1 and 1:10. Generally the hydroformylation is carried out with a rhodium concentration between $1\times10^{-2}$ and $5\times10^{-5}$, preferably between $5\times10^{-3}$ and $1\times10^{-4}$ gram atoms of rhodium per mole of 3-methylmercapto-1-acetoxy-propene-1 employed. These ratios cause optimum reaction speeds and yields.

The rhodium complexes suitable for the process of the invention contain organic compounds of trivalent phosphorus as ligands, in which case the ligands are used in excess. The production of such complex compounds is described in the literature and for example, can be carried out by combining a rhodium salt of an organic acid in liquid phase with the ligands, for example, triphenylphosphine or triphenyl phosphite. The catalyst can also be produced from the carbonyl complexes of rhodium, e.g. starting from $Rh_2(CO)_8$ or $Rh_6(CO)_{16}$ and forming the catalyst by heating with the desired ligands. Furthermore, there can also be employed preformed rhodium complexes such as $HRh(CO)(PPh_3)_3$ or $ClRh(PPh_3)_3$ where Ph indicates a phenyl group. Finally there can also be used ionic complexes having the rhodium containing cation and an anion not supporting the coordination such as $BPh_4^-$, $BF_4^-$, $ClO_4^-$, $PF_6^-$ or $NO_3^-$.

Preferred ligands are tri($C_1$-$C_{30}$)-alkylphosphines such as trioctylphosphine, tridodecylphosphine, trimethylphosphine, tributylphosphine, triisooctylphosphine, trihexadecylphosphine, dimethyl butyl phosphine, trieicosanylphosphine, aryl, or alkarylphosphines, especially phenyl or alkylphenyl phosphines such as triphenylphosphine, tritolylphosphine, e.g. tri p-tolylphosphine or tri o-tolylphosphine, tri 4-ethylphenylphosphine, tri-xylylphosphine, tri-$C_1$-$C_{30}$-alkyl phosphites, such as trimethyl phosphite, triethyl phosphite, trioctyl phosphite, dimethyl ethyl phosphite, tris(2-ethylhexyl) phosphite, tris decyl phosphite, tris isodecyl phosphite, tri dodecyl phosphite, trihexadecyl phosphite, tris eicosanyl phosphite, or aryl phosphites such as triphenyl phosphite, tri p-tolyl phosphite, tri o-tolyl phosphite, tri xylyl phosphite, or mixed aryl alkyl phosphites such as phenyl dimethyl phosphite.

The ligands are added in excess over the rhodium in order to suppress undesired side reactions, for example isomerization reactions, and to obtain maximum yields of the desired 4-methylmercapto-1-acetoxybutyraldehyde. Besides by using an excess of ligand the stability of the catalyst is improved. A molar ratio of ligand: rhodium between 5:1 and 150:1 is suitable.

The hydroformylation reaction can be carried out in a simple pressure vessel in discontinuous (batch) or continuous manner. The pressure generally is between 10 and 300 bar, preferably between 30 and 200 bar. The reaction temperature is generally between 50° and 180° C., preferably between 70° and 120° C.

Basically the hydroformylation can also be carried out without solvent, but it is more advantageous to carry it out in the presence of a solvent. Suitable solvents especially are aliphatic and aromatic hydrocarbons, e.g. hexane, octane, decane, benzene, toluene, or xylene. Suitably the solvent is employed in about an equal amount by weight of the 3-methylmercapto-1-acetoxy-propene-1 to be reacted. However, it is also possible to use a larger amount of solvent. The co-use of a solvent increases the selectivity of the hydroformylation reaction in the direction of the desired 4-methylmercapto-2-acetoxy-butyraldehyde.

After the reaction the 4-methylmercapto-2-acetoxybutyraldehyde formed can be isolated by fractional distillation. The catalyst remaining in the distillation residue, as well as the solvent if it is used, can be returned again to the hydroformylation reaction. The 4-methylmercapto-2-acetoxy-butyraldehyde can be subjected to a second fractional distillation for further purification.

The invention will be more clearly explained by the following examples. Unless otherwise indicated all percentages and parts are by weights.

The process can comprise, consist essentially of, or consist of the stated steps with the recited materials.

EXAMPLE 1

There were mixed together in a 640 ml shaking autoclave made of stainless steel 121.6 grams (0.83 mole) of 3-methylmercapto-1-acetoxy-propene-1, 1.1 grams of HRh(CO)(PPh$_3$)$_3$, 4.8 grams of triphenylphosphine and 180 ml of benzene. The autoclave was flushed with synthesis gas. Subsequently the charge was hydroformylated at a temperature of 110° C. and a pressure of 80 bar with H$_2$/CO in a ratio of 1:1 for 5 hours. The pressure was maintained during the reaction by repressuring between 70 and 80 bar. The benzene was distilled off from the reaction mixture in a water jet vacuum. In the distillation of the residue in an oil pump vacuum 105.2 grams of 4-methylmercapto-2-acetoxy-butyraldehyde (72% of theory) passed over at 75°–80° C. at 0.1 mbar.

Elemental Analysis: C$_7$H$_{12}$O$_3$S

Calculated: C 47.71%; H 6.86%; S 18,19%. Found: C 47,92%; H 7,1%; S 18,4%.

IR-Spectrum (Film):

2920 cm$^{-1}$; 2840 cm$^{-1}$; 2730 cm$^{-1}$; 1750 cm$^{-1}$; 1735 cm$^{-1}$; 1430 cm$^{-1}$; 1370 cm$^{-1}$; 1235 cm$^{-1}$; 1100 cm$^{-1}$; 1050 cm$^{-1}$.

$^1$H-NMR-Spectrum (CDCl$_3$): δ=2,05 (s, 3 H): —S—C$\underline{H}_3$ δ=2,20 (s, 3 H): —OCO—C$\underline{H}_3$ δ=2,3–2,7 (m, 4 H): —C$\underline{H}_2$—C$\underline{H}_2$— δ=5,15 (t, 1 H): —C$\underline{H}$—CHO δ=9,64 (s, 1 H): —C$\underline{H}$O

EXAMPLE 2

Example 1 was repeated with a pressure of only 50 bar of H$_2$/CO. After the working up there were obtained 95.0 grams (65% of theory) of 4-methylmercapto-2-acetoxy-butyraldehyde.

EXAMPLE 3

Example 1 was repeated but using 5 grams of triphenyl phosphite in place of the triphenylphosphine. After the working up there were obtained 101.2 grams (69% of theory) of 4-methylmercapto-2-acetoxy-butyraldehyde.

EXAMPLE 4

Example 1 was repeated with a CO/H$_2$ pressure of 150 bar. After the working up there were obtained 112.6 grams (77% of theory) of 4-methylmercapto-2-acetoxy-butyraldehyde.

EXAMPLE 5

There were mixed together in a 450 ml shaking autoclave made of stainless steel 47 grams (0.32 mole) of 3-methylmercapto-1-acetoxy-propene-1, 0.7 grams (0.86 mole) of [Rh(COD)(PPh$_3$)$_2$] BF$_4$ (where COD is cyclooctadiene), 2.25 grams of triphenyl phosphine and 50 ml of toluene. Subsequently the charge was hydroformylated at a temperature of 110° C. and a pressure of 75 bar with a hydrogen-carbon monoxide gas mixture (1:1). The toluene was distilled off from the reaction mixture in a water jet vacuum. In the distillation of the residue in an oil pump vacuum there were obtained 41.4 grams (73% of theory) of 4-methylmercapto-2-acetoxy-butyraldehyde.

EXAMPLE 6

In a manner analogous to Example 5, 44 grams (0.30 mole) of 3-methylmercapto-1-acetoxy-propene-1 were hydroformylated with the catalyst residue of Example 5. There were obtained 37.5 grams (71% of theory) of 4-methylmercapto-2-acetoxy-butyraldehyde.

What is claimed is:

1. 4-methylmercapto-2-acetoxy-butyraldehyde of the formula

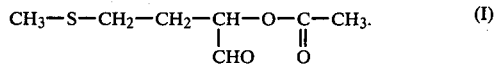
(I)